(12) United States Patent
Woznica et al.

(10) Patent No.: US 6,645,914 B1
(45) Date of Patent: Nov. 11, 2003

(54) SURFACTANT-AMMONIUM SULFATE ADJUVANT COMPOSITION FOR ENHANCING EFFICACY OF HERBICIDES

(75) Inventors: Zenon J. Woznica, Fargo, ND (US); John Nalewaja, Fargo, ND (US); Calvin Messersmith, Fargo, ND (US); Edward Szelezniak, Fargo, ND (US)

(73) Assignee: NDSU-Research Foundation, Fargo, ND (US)

( * ) Notice: Subject to any disclaimer, the term of this patent is extended or adjusted under 35 U.S.C. 154(b) by 0 days.

(21) Appl. No.: 10/139,000

(22) Filed: May 1, 2002

(51) Int. Cl.[7] .................. A01N 25/30; A01N 57/02; B01F 17/28
(52) U.S. Cl. ................... 504/206; 504/365; 516/203
(58) Field of Search ..................... 504/206, 365; 516/203

(56) References Cited

U.S. PATENT DOCUMENTS

| | | | | |
|---|---|---|---|---|
| 5,356,861 A | | 10/1994 | Gednalski et al. | 504/206 |
| 5,563,112 A | * | 10/1996 | Barnes III | 504/123 |
| 5,668,085 A | | 9/1997 | Forbes et al. | 504/206 |
| RE36,149 E | | 3/1999 | Gednalske et al. | 504/206 |
| 5,928,993 A | * | 7/1999 | Johansson | 504/116 |
| 6,228,807 B1 | | 5/2001 | Kuchikata et al. | 504/206 |
| 6,364,926 B1 | | 4/2002 | Gryzik et al. | 71/64.1 |

* cited by examiner

*Primary Examiner*—S. Mark Clardy
(74) *Attorney, Agent, or Firm*—Fitch, Even, Tabin & Flannery

(57) ABSTRACT

The present invention is directed to liquid homogenous adjuvant blends that include a liquid iminodipropionate amphoteric surfactant, ammonium sulfate and water. The liquid homogenous adjuvant blends are used in spray carrier containing herbicides for conytrol of weeds or other undesired vegetation.

11 Claims, No Drawings

US 6,645,914 B1

SURFACTANT-AMMONIUM SULFATE ADJUVANT COMPOSITION FOR ENHANCING EFFICACY OF HERBICIDES

STATEMENT OF GOVERNMENT RIGHTS

The U.S. Government has a paid-up license in this invention and the right in limited circumstances to require the patent owner to license others on reasonable terms as provided for by the terms of Grant Nos. 97-34361-3960, 98-34361-6831 and 99-34361-8432 awarded by the U.S. Department of Agriculture.

This invention relates to a homogeneous adjuvant blend for use in spray carriers containing herbicides, which are used to control weeds or other undesired vegetation. More specifically, the homogeneous adjuvant blend of the invention includes a blend of liquid iminodipropionate amphoteric surfactant, ammonium sulfate and water.

BACKGROUND

Herbicides used to control weeds or undesired vegetation in agriculture may be applied by postemergence spraying of a herbicide on the crop. The spray mixture for herbicide application usually contains an effective amount of known herbicide along with adjuvants and water. The adjuvants are commonly added to herbicidal spray mixtures to enhance postemergence weed control and/or to reduce spray drift during herbicide application.

Adjuvant surfactants provide increased spray retention on the leaf surface and increased herbicide absorption into the plant. However, surfactant(s) alone often are not able to increase herbicide efficacy, especially when hard or very hard water is used as a spray carrier. Ammonium sulfate overcomes the antagonistic effect of sodium, calcium and magnesium ions from hard water. Further, ammonium ions from ammonium sulfate may increase herbicide absorption. The mixture of surfactant(s) and ammonium sulfate is often a beneficial combination that increases efficacy of herbicides, mainly glyphosate and other weak acid herbicides.

Ammonium sulfate is a common solid fertilizer. The commercial fertilizer often lacks purity and causes sprayer nozzle plugging and thus non-uniform spray distribution and weed control efficacy. Spray-grade solid (dry) ammonium sulfate products are available that have reduced the sprayer nozzle plugging problems. Both a surfactant and ammonium sulfate usually are required to maximize efficacy of postemergent herbicides.

Surfactant adjuvants are sold commercially for use with herbicides and most are physically compatible with ammonium sulfate when dilute with water in a sprayer tank. However, specific surfactants are required for maximum efficacy when used in combination with ammonium sulfate and the wrong surfactant can even reduce efficacy. There are a large number of surfactant products available, so it is difficult for growers to know the most effective product for use with ammonium sulfate. A formulated adjuvant containing both surfactant and ammonium sulfate is desired by growers to assure efficacy, to reduce the number products for storage, and to minimize errors associated with mixing two or more products during herbicide spray preparation.

The combination of an effective surfactant with ammonium sulfate in a concentrated formulation would be logical. However, until now, only the alkyl polysaccharide surfactants have been compatible with ammonium sulfate in a concentrated adjuvant formulation, as described in U.S. Pat. Nos. 5,356,861 and RE 36,149. These surfactants, selected mainly because of physical compatibility with ammonium sulfate, may not maximize efficacy with herbicides.

Glyphosate (N-phosphonomethylglycine) is well known in the art and is a widely used herbicide for postemergence, nonselective weed control. Most herbicides, including glyphosate, are applied in a water carrier. To be effective, the spray mixture must be retained on a weed leaf surface; the herbicide active ingredient must be absorbed by the plant; and the herbicide must be translocated to the site of action.

Many cations present in a spray carrier, usually water, antagonize the efficacy of glyphosate and other weak acid herbicides formulated as salts, e.g., 2,4-D [(2,4-dichlorophenoxy)acetic acid], MCPA [(4-chloro-2-methylphenoxy)acetic acid], dicamba (3,6-dichloro-2-methoxybenzoic acid), and bentazon [3-(1-methylethyl)-(1H)-2,1,3-benzothiadiazin-4(3H)-one 2,2-dioxide]. To increase spray droplet retention on the weed surface, to enhance absorption into the plant, and to overcome the antagonistic effect of cations present in the spray carrier, glyphosate and other weak acid herbicides are often applied with an adjuvant.

Typically commercial glyphosate formulations contain an adjuvant, usually a surfactant. However, the amount of surfactant in commercial glyphosate formulations often is not sufficient to optimize efficacy and does not prevent antagonism from spray-carrier cations. Thus, additional surfactant and/or ammonium sulfate often are recommended. In practice, the additional surfactant and/or ammonium sulfate and herbicide are added separately to the sprayer tank during spray mixture preparation.

U.S. Pat. No. 6,228,807 refers to dry herbicidal compositions containing one or more herbicides plus surfactant, ammonium sulfate, and other ingredients. As described in the '807 patent, the adjuvants are not added separately into the tank but concomitant with a defined rate of herbicide. Because the recommended rate of herbicide changes depending on crops, weed species, and environment, the rate of surfactant and ammonium sulfate adjuvants applied with such dry herbicidal composition will change directly with the herbicide rate and may not be in a proper amount to provide optimum herbicide efficacy. This is especially important when a herbicide is used at a low rate. As described in the '807 patent, the amount of adjuvant applied is automatically reduced when the herbicide formulation is used at a low rate, so the adjuvant concentration may be too low for spray retention and to overcome antagonistic effect of minerals in the spray water. In fact, low herbicide rates typically require a comparatively high adjuvant concentration to attain acceptable herbicide efficacy.

SUMMARY

The present invention is directed to a liquid adjuvant blend that is homogeneous and which is particularly useful for improving the efficacy of the herbicide glyphosate. The liquid adjuvant blend is used as a tank mixture, where the liquid adjuvant blend is added to a sprayer tank as a separate product along with water and herbicide. The amount of liquid adjuvant blend added to the sprayer tank may be adjusted independent of the herbicide rate to take into account water hardness, weed species, spray volume, and environmental conditions.

The liquid homogeneous adjuvant blend of the invention includes from about 10 to about 25 weight to volume percent of an iminodipropionate amphoteric surfactant. In this aspect of the invention, the iminodipropionate amphoteric surfactant is selected from the group consisting of C12-15 alkyloxypropyl-3-iminodipropionic acid, mono(sodium or potassium or ammonium) salt, decyloxypropyl-3-iminodipropionic acid, mono(sodium or potassium, or ammonium) salt {alternate name: beta.-alanine, N-(2-carboxyethyl)-N-[3-(decyloxy)propyl]-,mono(sodium or potassium or ammonium) salt}, and mixtures thereof. The liquid homogeneous adjuvant blend of the invention further includes from about 15 to about 36 weight-to-volume percent ammonium sulfate. The remaining volume of the adjuvant blend is water.

Optionally, this adjuvant composition may also include a drift retardant, dye, humectant, corrosion inhibitor, microbial inhibitor, pH adjuster, anti-foam agent, and mixture thereof. Also, the adjuvant could be mixed with glyphosate or other herbicide(s) to form a liquid complete herbicide-adjuvant formulation.

In another aspect, when needed for weed control purposes, about 1 to about 2 percent of the liquid adjuvant blend of the present invention is blended with water and an effective amount of herbicide to provide a postemergence herbicidal aqueous spray composition. In this aspect of the invention, the herbicidal spray composition typically includes about 95 to about 98 percent water, about 1 to about 4 percent herbicide, and about 1 to about 2 percent of the adjuvant of the present invention, based on weight of the total herbicidal spray composition. In an important aspect of the invention, the preferable herbicide used in the herbicidal spray composition is glyphosate.

In another aspect, the present invention provides a method for controlling weeds by applying a postemergence herbicidal spray composition to weeds and/or other undesired vegetation. The herbicidal aqueous spray composition includes iminodipropionate amphoteric surfactant, ammonium sulfate, and herbicide as described above.

DETAILED DESCRIPTION

Definintons

In an important aspect, the present invention provides a liquid adjuvant that is homogeneous and stable. As used herein a "homogeneous and stable" formulation means that all components of the adjuvant composition when mixed together form a clear, continuous blend that does not separate during storage at temperatures between 0° C. and 500° C. for at least about 180 days.

In another important aspect of the invention, the liquid adjuvant is compatible with various qualities of water. Even where the liquid adjuvant of the invention is blended with moderate, hard or very hard water, the liquid adjuvant remains homogeneous and stable. The use of moderate, hard or very hard water with the liquid adjuvant blend and herbicide provides a herbicide efficacy that is similar to the efficacy of the same liquid adjuvant and herbicide blended with soft water. Water described as "hard" is high in dissolved minerals, specifically calcium and magnesium. The degree of hardness becomes greater as the calcium and magnesium content increases. Hardness of water as defined by the U.S. Geological Survey is described as follows:

| Water | Water hardness expressed as CaCO$_3$ in mg/L* |
|---|---|
| Soft | 0–60 |
| Moderate | 61–120 |
| Hard | 121–180 |
| Very hard | More than 180 |

*Water hardness as CaCO$_3$ (mg/L) = 2.5 [Ca$^{2+}$ (mg/L) + 4.1 [Mg$^{2+}$ (mg/L)]

In a very important aspect of the invention, liquid adjuvant blended with water having up to 500 mg/L Ca and Mg remained homogeneous and stable and provided a herbicide efficacy that was similar to the efficacy of the same liquid adjuvant and herbicide blended with soft water.

Liquid Amphoteric Iminodipropionate Surfactant

Liquid amphoteric surfactants useful in the present invention are from the iminodipropionate group, e.g., products from Tomah Products Inc.: C12-15 alkyloxypropyl-3-iminodipropionic acid, monosodium salt (trade name Amphotheric N), decyloxypropyl-3-iminodipropionic acid, monosodium salt (trade name Alkali Surfactant NM) and other iminodipropionates from Tomah Product Inc. (e.g., Amphoteric NM.RTM). Salts other than the sodium salt of these surfactants also may be used, e.g., ammonium and potassium salts of these surfactants.

Thus, the surfactants used in the present invention are not amino oxides or betaines as described in U.S. Pat. No. 6,228,807 and are not nonionic surfactants, particularly alkyl polysaccharides, as described in U.S. Pat. No. 5,356,861 and RE 36,149.

Ammonium Sulfate

Ammonium sulfate component useful in the present invention is commercially available solid or liquid product containing between 20 to 100 percent of ammonium sulfate, and preferably is spray grade.

Application of Homogeneous Adjuvant Blend

The homogeneous adjuvant blend is customarily formulated and sold in two and one half (2.5) gallon or larger containers. The adjuvant blend is used to make up the spray mixture, which also includes spray water (about 95% to about 98%) and a herbicidally effective amount of a postemergence herbicide, customarily 4% or less by weight of the aqueous spray mixture. The herbicide is customarily added to the water at the recommended label amount; for example, glyphosate typically is applied in an amount effective for providing an application rate of from about 0.5 to about 4 pounds per acre of the herbicide active ingredient. In this aspect of the invention, the spray applied to the plants is typically:

about 1 to 2 weight percent adjuvant, preferably 1 weight percent with soft and moderate water and 2 weight percent with hard and very hard water;

about 1 to about 4 weight percent herbicide; and the remainder of the spray being water. All weight percents are based on weight of the total herbicidal spray composition.

Preferably, the herbicide utilized with this invention is glyphosate and other weak acid herbicides, e.g., consisting of 2,4-D [(2,4-dichlorophenoxy)acetic acid], MCPA [(4-chloro-2-methylphenoxy)acetic acid], dicamba (3,6-dichloro-2-methoxybenzoic acid), bentazon [3-(1-methylethyl)-(1H)-2,1,3-benzothiadiazin-4(3H)-one 2,2-dioxide], glufosinate [2-amino-4-(hydroxymethylphosphinyl) butanoic acid], and mixtures thereof.

The following examples illustrate methods for carrying out the invention and should be understood to be illustrative of, but not limiting upon, the scope of the invention, which is defined in the appended claims.

EXAMPLES

Example 1

Preparation of liquid Adjuvant Blend (Composition 1) Based on Amphoteric Surfactant Decyloxypropyl-3-iminodipropionic Acid, Monosodium Salt (Alkali Surfactant NM.RTM):

| | | |
|---|---|---|
| 1. | Decyloxypropyl-3-iminodipropionic acid, monosodium salt | 15.75 weight percent |
| 2. | Ammonium sulfate | 31.00 weight percent |
| 3. | Water | 53.25 weight percent |

For example, to prepare 1 kilogram of the above adjuvant blend, the following method and ingredients were used:
1. 450 grams of Alkali Surfactant NM.RTM (35 percent active ingredient) was weighed.
2. 400 grams of liquid ammonium sulfate (40 weight percent solution) was added.
3. 150 grams of dry (crystalline) ammonium sulfate was added.

All ingredients were mixed in a 2-L glass jar using a magnetic stirrer until the crystalline ammonium sulfate was completely dissolved and the adjuvant formulation became homogeneous. Mixing process occurred at about 120° F. All ingredients formed a clear, homogeneous adjuvant blend without any tendency for separation in a temperature range between 32° F. to 122° F. over a period of at least 180 days.

This adjuvant composition was added at 1 or 2 percent by volume to various herbicide spray mixtures, and gave enhancement of activity on plants that was superior to commercial adjuvants, especially when hard water was used as a spray carrier.

Example 2

Glyphosate Efficacy and Effect of Adjuvants on Glyphosate-resistant Soybean and Corn Materials and Methods Wheat (Triticum aestivum L.), velvetleaf (Abutilion theophrasti Medicus), Roundup Ready.RTM soybean (Glycine max (L.) Merr.), and Roundup Ready.RTM corn (Zea mays L.) were grown in plastic cones containing a commercial peat-based greenhouse mixture. Plants were thinned 1 wk after emergence to seven wheat, three velvetlaf, or one corn or soybean per cone and were watered and fertilized as needed for healthy growth. Natural daylight was supplemented for 16 h photoperiod with metal halide lamps with the light intensity of 450 $\mu E/m^2/s$. The greenhouse was maintained at 20° C. at night and 25 ±5° C. during the day. Glyphosate with adjuvants was applied to three-leaf wheat and corn, first-pair leaf velvetleaf, and to first-trifoliolate-leaf soybean using a cabinet laboratory sprayer that delivered 80 L/ha through a 8001 flat fan nozzle at 280 kPa generated by compressed air. Distilled water, Fargo tap water (soft), and two well waters from the Devils Lake, ND, area (hard and high sodium content, respectively) were used as spray carriers. Ion concentrations in these waters are described in TABLE 1. Formulation type and rates of glyphosate and adjuvants are specified in each table. In all greenhouse studies, plants were evaluated for herbicide injury and adjuvant efficacy 14 days after herbicide application. Data presented are the means of two experiments with four replicates per experiment.

TABLE 1

Ion concentration in waters used in experiments with glyphosate.

| Water source | $Ca^{2+}$ | $Mg^{2+}$ | $Na^+$ | K+ | —$CO_3$ | —$HCO_3$ | —Cl | $^{-2}SO_4$ |
|---|---|---|---|---|---|---|---|---|
| | mg/L | | | | | | | |
| Distilled | 3 | 0 | 1 | 0 | 0 | 1 | 1 | 1 |
| Fargo, ND (tap) | 30 | 8 | 59 | 6 | 4 | 8 | 23 | 144 |
| Devils Lake, ND No.1 (well) | 240 | 293 | 173 | 120 | 0 | 452 | 82 | 1777 |
| Devils Lake, ND No.2 (well) | 22 | 7 | 893 | 13 | 18 | 708 | 277 | 1029 |

The adjuvants, ammonium sulfate, Activator 90. RTM, and mixtures thereof, Surfate.RTM, and Composition 1 were added into water [weight (for solids) or volume (for liquids) per volume concentrations shown in TABLE 2] with glyphosate at 100 g ae/ha to prepare the final aqueous spray mixture applied at 80 L/ha on 2 to 3 leaf wheat. Calcium chloride was added to distilled water to get 0, 125, 250, and 500 mg/L calcium cations. TABLE 2 includes the results of assessment made 2 weeks after treatment.

Efficacy of glyphosate applied alone or with surfactant Activator 90. RTM was strongly reduced as the calcium concentration in water increased. However, Composition 1 adjuvant of present invention, especially applied at 2 volume percent completely overcame glyphosate antagonism caused even by 500 mg/L of calcium cations in the spray mixture.

TABLE 2

Wheat fresh weigh reduction from glyphosate at 100 g ae/ha (Roundup Ultra Max.RTM) as influenced by adjuvants and calcium cations.

| Adjuvant and concentration | $Ca^{2+}$ (mg/L)* | | | |
|---|---|---|---|---|
| | 0 | 125 | 250 | 500 |
| | % fresh weight reduction | | | |
| None | 27 | 2 | 1 | 9 |
| Ammonium sulfate 1% | 65 | 72 | 73 | 64 |
| Activator 90.RTM 0.5% | 31 | 17 | 19 | 18 |
| Activator 90.RTM 0.5% + ammonium sulfate 1% | 47 | 54 | 11 | 14 |
| Surfate.RTM 1% | 72 | 72 | 73 | 50 |
| Surfate.RTM 2% | 76 | 76 | 72 | 66 |
| Composition 1 1% | 74 | 80 | 74 | 49 |
| Composition 1 2% | 75 | 76 | 84 | 79 |
| LSD (0.05) | 9 | | | |

*$Ca^{2+}$ from calcium chloride

Roundup Ultra Max.RTM is a glyphosate formulation containing adjuvant from Monsanto Company; Activator 90. RTM is a nonionic surfactant of alkylpolyoxyethylene ethers and free fatty acids from Loveland Industries; Surfate.RTM is a nonionic surfactant and ammonium sulfate blend from AGSCO Inc.; Composition 1 is an experimental adjuvant blend, which refers to present invention consisting of surfactant decyloxypropyl-3-iminodipropionic acid, monosodium salt (15.75%), ammonium sulfate (31%), and water (53.25%).

The adjuvants, Activator 90. RTM, MON 0818, Atplus GTM7, Atplus GTM10 and their mixtures with ammonium sulfate, Surfate.RTM, and Composition 1 were added into three water carriers [weight (for solids) or volume (for liquids) per volume concentrations shown in TABLE 3] with glyphosate (100 g ae/ha) to prepare the final aqueous spray mixture applied at 80 L/ha on 2 to 3 leaf wheat. Ion concentrations in water carriers is shown in TABLE 1. TABLE 3 includes the results of assessment made 2 weeks after treatment.

Efficacy of glyphosate applied alone or with surfactants was strongly antagonized by salts presented in both well waters from Devils Lake, N. Dak., and addition of ammonium sulfate was needed to overcome this glyphosate antagonism. However, Composition 1 adjuvant of present invention strongly increased glyphosate efficacy and at 2 percent completely overcame glyphosate antagonism from salts present in the water carriers.

TABLE 3

Wheat fresh weigh reduction from glyphosate at 100 g ae/ha (Roundup Ultra Max.RTM) as influenced by adjuvants and different water carrier sources.

| Adjuvants and concentrations | Water source | | |
|---|---|---|---|
| | Fargo, ND (tap) | Devils Lake, ND No. 1 (well) | Devils Lake, ND No. 2 (well) |
| | % fresh weight reduction | | |
| None | 40 | 29 | 17 |
| Activator 90.RTM 0.5% | 10 | 10 | 14 |

TABLE 3-continued

Wheat fresh weigh reduction from glyphosate at 100 g ae/ha (Roundup Ultra Max.RTM) as influenced by adjuvants and different water carrier sources.

| Adjuvants and concentrations | Water source | | |
|---|---|---|---|
| | Fargo, ND (tap) | Devils Lake, ND No. 1 (well) | Devils Lake, ND No. 2 (well) |
| | % fresh weight reduction | | |
| Activator 90.RTM 0.5% + ammonium sulfate 1% | 58 | 56 | 54 |
| MON 0818 0.5% | 75 | 61 | 14 |
| MON 0818 0.5% + ammonium sulfate 1% | 76 | 78 | 67 |
| Atplus GTM7.RTM 0.5% | 63 | 59 | 16 |
| Atplus GTM7.RTM 0.5% + ammonium sulfate 1% | 78 | 83 | 79 |
| Atplus GTM10.RTM 0.5% | 51 | 54 | 15 |
| Atplus GTM10.RTM 0.5% + ammonium sulfate 1% | 68 | 81 | 80 |
| Surfate.RTM 1% | 75 | 83 | 59 |
| Surfate.RTM 2% | 79 | 87 | 67 |
| Composition 1 1% | 74 | 80 | 67 |
| Composition 1 2% | 78 | 82 | 72 |
| LSD (0.05) | 8 | | |

Roundup Ultra Max.RTM is a glyphosate formulation containing adjuvant from Monsanto Company; Activator 90. RTM is a nonionic surfactant of alkylpolyoxyethylene ethers and free fatty acids from Loveland Industries; MON 0818 is ethoxylated tallow amine cationic surfactant from Monsanto Company; Atplus GTM7. RTM and Atplus GTM10.RTM are proprietary adjuvants for glyphosate from Uniqema (ICI Surfactants); Surfate.RTM is a nonionic surfactant and ammonium sulfate blend from AGSCO Inc.;

Composition 1 is an experimental adjuvant blend, which refers to present invention consisting of surfactant decyloxypropyl-3-iminodipropionic acid, monosodium salt (15.75%), ammonium sulfate (31%), and water (53.25%).

The adjuvants, ammonium sulfate, Activator 90.RTM, and mixtures thereof, Surfate.RTM, and Composition 1 were added into two water carriers (weight [for solids] or volume [for liquids] per volume concentrations shown in TABLE 4) with three glyphosate formulations, all at 125 g ae/ha, to.prepare the final aqueous spray mixture applied at 80 L/ha on 2 to 3 leaf wheat. Ion concentrations in water carriers are shown in TABLE 1. TABLE 4 includes the results of assessment made 2 weeks after treatment.

Efficacy of glyphosate applied alone or with surfactant only, regardless of herbicide formulation, was low and was antagonized by hard water from Devils Lake, ND. Addition of ammonium sulfate with the surfactant did not overcome glyphosate antagonism. However, Composition 1 adjuvant of present invention strongly increased glyphosate efficacy and overcame glyphosate antagonism from salts present in the hard water carrier.

TABLE 4

Wheat fresh weigh reduction from various glyphosate formulations at 125 g ae/ha as influenced by adjuvants and different water carrier sources.

| | Glyphosate formulations | | | | | |
|---|---|---|---|---|---|---|
| | Roundup Ultra Max.RTM | | Touchdown .RTM | | Roundup Custom.RTM | |
| | Water sources | | | | | |
| Adjuvant and concentration | Fargo (tap) | Devils Lake No. 1 (well) | Fargo (tap) | Devils Lake No. 1 (well) | Fargo, (tap) | Devils Lake No. 1 (well) |
| | % fresh weight reduction | | | | | |
| None | 19 | 16 | 22 | 16 | 34 | 24 |
| Ammonium sulfate 1% | 54 | 43 | 71 | 24 | 68 | 23 |
| Activator 90.RTM 0.5% | 24 | 15 | 26 | 21 | 21 | 22 |
| Activator 90.RTM 0.5% + ammonium sulfate 1% | 39 | 21 | 36 | 27 | 35 | 38 |
| Composition 1 1% | 81 | 77 | 71 | 76 | 77 | 68 |
| Composition 1 2% | 76 | 75 | 76 | 75 | 84 | 71 |
| Surfate.RTM 1% | 73 | 67 | 72 | 75 | 77 | 63 |
| Surfate.RTM 2% | 81 | 72 | 75 | 84 | 79 | 72 |
| LSD (0.05) | | | 9 | | | |

Roundup Ultra Max.RTM is a glyphosate formulation containing adjuvant from Monsanto Company; Touchdown.RTM is a glyphosate formulation containing adjuvant from Syngenta; Roundup Custom.RTM is a glyphosate formulation without adjuvant from Monsanto Company; Activator 90. RTM is a nonionic surfactant of alkylpolyoxyethylene ethers and free fatty acids from Loveland Industries; Surfate.RTM is a nonionic surfactant and ammonium sulfate blend from AGSCO Inc.; Composition 1 is an experimental adjuvant blend, which refers to present invention consisting of surfactant decyloxypropyl-3-iminodipropionic acid, monosodium salt (15.75%), ammonium sulfate (31%), and water (53.25%).

Various iminodipropionate, betaine, imidazoline, and amine oxide amphoteric surfactants applied with ammonium sulfate and adjuvant formulations containing surfactant and ammonium sulfate, including Composition 1 of present invention, were added into hard water carrier [weight (for solids) or volume (for liquids) per volume concentrations shown in TABLE 5] with glyphosate at 125 g ae/ha to prepare the final aqueous spray mixture applied at 80 L/ha on 2 to 3 leaf wheat. Ion concentration in water carrier is shown in TABLE 1. TABLE 5 includes the results of assessment made 2 weeks after treatment.

All adjuvants increased glyphosate efficacy. However, the iminodipropionate amphoteric surfactant and, Composition 1 of. present invention that contains iminodipropionate amphoteric surfactant increased efficacy of glyphosate the most and were superior to amphoteric surfactants containing betaine, imidazoline, or amine oxide and commercial adjuvants containing nonionic surfactant and ammonium sulfate.

TABLE 5

Wheat fresh weigh reduction from glyphosate (Roundup Ultra Max.RTM) at 125 g ae/ha applied with hard water (Devils Lake, ND, No. 1 - well water) as influenced by adjuvants.

| Adjuvant and concentration | Fresh weight reduction % |
|---|---|
| None | 13 |
| Amphoteric N.RTM 0.25% + ammonium sulfate 0.25% | 51 |
| Alkali Surfactant NM.RTM 0.25% + ammonium sulfate 0.25% | 72 |
| Amphoteric LH.RTM 0.25% + ammonium sulfate 0.25% | 72 |
| Amphoteric L.RTM 0.25% + ammonium sulfate 0.25% | 42 |
| Miranol C2M-SF Conc.RTM 0.25% + ammonium sulfate 0.25% | 47 |
| Miranol BM Conc.RTM 0.25% + ammonium sulfate 0.25% | 61 |
| Lonzaine CS.RTM 0.25% + ammonium sulfate 0.25% | 51 |
| Lonzaine C.RTM 0.25% + ammonium sulfate 0.25% | 55 |
| Aromox C/12.RTM 0.25% + ammonium sulfate 0.25% | 48 |
| Composition 1 1% | 71 |
| Surfate.RTM 1% | 60 |
| Class Act Next Generation.RTM 1% | 64 |
| LSD (0.05) | 11 |

Roundup Ultra Max.RTM is a glyphosate formulation containing adjuvant from Monsanto Company; Amphoteric N.RTM, Alkali Surfactant NM.RTM, and Amphoteric LH.RTM are iminodipropionate amphoteric surfactants from Tomah Products Inc.; Amphoteric LH.RTM is betaine amphoteric surfactant from Tomah Products Inc.; Miranol C2M-SF Conc.RTM is imidazolines and imidazoline derivatives amphoteric surfactant from Rhodia, Inc.; Miranol BM Conc.RTM is monocarboxylic lauric/myrystic derivative, sodium salt amphoteric surfactant from Rhodia, Inc.; Lonzaine CS.RTM is cocamido sulfobetaine amphoteric surfactant from Lonza, Inc.; Lonzaine C.RTM is betaine amphoteric surfactant from Lonza, Inc.; Aromox C/12.RTM is amine oxide amphoteric surfactant from Agzo Nobel Chemicals Inc.; Surfate.RTM is a nonionic surfactant and ammonium sulfate blend from AGSCO Inc.; Class Act Next Generation.RTM is a nonionic surfactant and ammonium sulfate blend from Agriliance; Composition 1 is an experimental adjuvant blend, which refers to present invention consisting of surfactant decyloxypropyl-3-iminodipropionic acid, monosodium salt (15.75%), ammonium sulfate (31%), and water (53.25%).

The adjuvants, ammonium sulfate, Activator 90. RTM, and mixtures thereof, Surfate.RTM, and Composition 1 were added into a hard water carrier [weight (for solids) or volume (for liquids) per volume concentrations shown in TABLE 6] with glyphosate at 150 g ae/ha to prepare the final aqueous spray mixture applied at 80 L/ha on 2-leaf velvetleaf. Ion concentrations in the water carrier are shown in TABLE 1. TABLE 6 includes the results of assessment made 2 weeks after treatment.

All adjuvants increased efficacy of glyphosate. However, adjuvants containing surfactant and ammonium sulfate, including Composition 1 adjuvant of present invention, were more effective than ammonium sulfate and nonionic surfactant applied alone.

TABLE 6

Velvetleaf fresh weigh reduction from glyphosate (Roundup Ultra Max.RTM) at 150 g ae/ha applied with hard water (Devils Lake, ND, No. 2 - well water) as influenced by adjuvants.

| Adjuvant and concentration | Fresh weight reduction % |
|---|---|
| None | 40 |
| Ammonium sulfate 1% | 54 |
| Activator 90.RTM 0.5% | 54 |
| Activator 90.RTM + ammonium sulfate 0.5% + 1% | 70 |
| Surfate.RTM 2% | 64 |
| Composition 1 2% | 70 |
| LSD (0.05) | 11 |

Roundup Ultra Max.RTM is a glyphosate formulation containing adjuvant from Monsanto Company; Activator 90. RTM is a nonionic surfactant of alkylpolyoxyethylene ethers and free fatty acids from Loveland Industries; Surfate.RTM is a nonionic surfactant and ammoniumsulfate blend from AGSCO Inc.; Composition 1 is an experimental adjuvant blend, which refers to present invention consisting of surfactant decyloxypropyl-3-iminodipropionic acid, monosodium salt (15.75%), ammonium sulfate (31%), and water (53.25%).

Different formulations of glyphosate (Roundup Ultra Max.RTM, Touchdown.RTM, and Roundup Custom.RTM), all at 2.5 kg ae/ha, applied alone and with adjuvant Surfate.RTM at 1 and 2% and Composition 1 adjuvant of present invention at 1 and 2% did not cause any injury or plant height reduction of Roundup Ready.RTM soybean and Roundup Ready.RTM corn 7 and 14 days after treatment (data not presented). This glyphosate rate is at least two-fold greater than normal use rate in a crop.

Example 3

Efficacy of 2,4-D, Dicamba, and Bentazon as Influenced by Adjuvants

Materials and methods

Kochia (Kochia scoparia L.) was grown in plastic cones containing a commercial peat-based greenhouse mixture with 5 plants per cone. All growing conditions and herbicide application procedures were similar as explained in Example 2. Herbicides were applied to kochia at the 4 to 6-leaf stage. Herbicide formulation and rates of herbicides and adjuvants are specified in Table 7. Plants were evaluated for herbicide injury and fresh weight reduction 14 days after herbicide application. Data presented are the means of two experiments with four replicates per experiment.

The adjuvants, Activator 90. RTM and Composition 1, were added into soft and hard water carriers (volume per volume concentrations shown in TABLE 7) with 2,4-D at 220 g ae/ha, dicamba at 75 g ae/ha, or bentazon at 200 g ai/ha to prepare the final aqueous spray mixture applied at 80 L/ha on 4 to 6-leaf kochia. Ion concentrations in water carrier is shown in TABLE 1. TABLE 7 includes the results of assessment made 2 weeks after treatment.

All herbicides were antagonized by ions from hard water carrier. Composition 1 adjuvant of present invention increased efficacy of 2,4-D, dicamba, and bentazon and was superior to commercial adjuvant Activator 90. RTM, especially when hard water was used as a spray carrier.

TABLE 7

Kochia percent fresh weigh reduction from 2,4-D-dimethylamine salt (Amine 4 2,4-D Weed Killer.RTM) at 220 g ae/ha, dicamba-sodium salt (Banvel SGF.RTM) at 75 g ae/ha, and bentazone-sodium salt (Basagran.RTM) at 200 g ai/ha applied with soft water (Fargo, ND - tap water) and hard water (Devils Lake, ND, No. 2 - well water) as influenced by adjuvants.

| Adjuvant and concentration | Water source | |
|---|---|---|
| | Fargo, ND (tap) | Devils Lake No. 1 (well) |
| *2,4-D-dimethylamine salt* | | |
| None | 20 | 10 |
| Activator 90.RTM 0.5% | 27 | 21 |
| Composition 1 1% | 40 | 39 |
| LSD (0.05) | 8 | |
| *dicamba-sodium salt* | | |
| None | 12 | 9 |
| Activator 90.RTM 0.5% | 38 | 26 |
| Composition 1 1% | 42 | 48 |
| LSD (0.05) | 9 | |
| *bentazon-sodium salt* | | |
| None | 20 | 5 |
| Activator 90.RTM 0.5% | 74 | 64 |
| Composition 1 1% | 81 | 86 |
| LSD (0.05) | 8 | |

Amine 4 2,4-D Weed Killer.RTM is a dimethylamine salt formulation of 2,4-D from Platte Chemical Co.; Banvel SGF.RTM is a sodium salt formulation of dicamba from Micro Flo; Basagran.RTM is a sodium salt formulation of bentazon from BASF; Activator 90.RTM is a nonionic surfactant of alkylpolyoxyethylene ethers and free fatty acids from Loveland Industries; Composition 1 is an experimental adjuvant blend, which refers to present invention consisting of surfactant decyloxypropyl-3-iminodipropionic acid, monosodium salt (15.75%), ammonium sulfate (31w), and water (53.25%).

Numerous modifications and variations in practice of the invention are expected to occur to those skilled in the art upon consideration of the foregoing detailed description of the invention. Consequently, such modifications and variations are intended to be included within the scope of the following claims.

What is claimed is:

1. A liquid homogeneous adjuvant blend comprising:

from about 10 to about 25 weight to volume percent of a liquid iminodipropionate amphoteric surfactant selected from the group consisting of C12-15 alkyloxypropyl-3-iminodipropionic acid, mono (sodium or potassium or ammonium) salt, decyloxypropyl-3-iminodipropionic acid, mono (sodium or potassium, or ammonium) salt {alternate name: beta.-alanine,N-(2-carboxyethyl)-N-[3-(decyloxy)propyl], mono(sodium or potassium or ammonium) salt}, and mixtures thereof;

ammonium sulfate; and water.

2. The liquid homogeneous adjuvant blend of claim 1 wherein the blend includes from about 15 to about 36 weight to volume percent ammonium sulfate.

3. A herbicidal aqueous spray composition comprising:

a liquid iminodipropionate amphoteric surfactant selected from the group consisting of C12-15 alkyloxypropyl-3-iminodipropionic acid, mono(sodium or potassium or ammonium) salt, decyloxypropyl-3-iminodipropionic acid, mono (sodium or potassium, or ammonium) salt {alternate name: beta.-alanine,N-(2-carboxyethyl)-N-[3-(decyloxy)propyl], mono(sodium or potassium or ammonium) salt}, and mixtures thereof;

an effective amount of herbicide;

ammonium sulfate; and water.

4. The herbicidal aqueous spray composition according to claim 3 wherein the herbicidal spray composition includes from about 0.05 to about 0.5 weight percent iminodipropionate amphoteric surfactant, based on the weight of the final herbicidal spray composition.

5. The herbicidal aqueous spray composition according to claim 3 wherein the final herbicidal spray composition includes from about 0.3 to about 1 weight percent ammonium sulfate, based on the weight of the herbicidal spray composition.

6. The herbicidal aqueous spray composition according to claim 3 wherein the herbicidal spray composition includes from about 0.001 to about 4 weight percent glyphosate, based on the weight of the final herbicidal spray composition.

7. A method of controlling weeds which comprises applying a postemergence herbicidal spray composition to weeds and/or other undesired vegetation, the final herbicidal spray composition comprising:

a liquid iminodipropionate amphoteric surfactant selected from the group consisting of C12-15 alkyloxypropyl-3-iminodipropionic acid, mono(sodium or potassium or ammonium) salt, decyloxypropyl-3-iminodipropionic acid, mono(sodium or potassium, or ammonium) salt {alternate name: beta.-alanine, N-(2-carboxyethyl)-N-[3-(decyloxy)propyl], mono(sodium or potassium or ammonium) salt}, and mixtures thereof;

ammonium sulfate; and water;

an effective amount of glyphosate; and additional water to make up the final spray solution.

8. The method according to claim 7 wherein the herbicidal spray composition includes from about 0.05 to about 0.5 weight percent iminodipropionate amphoteric surfactant, based on the weight of the final herbicidal spray composition.

9. The method according to claim 7 wherein the herbicidal spray composition includes from about 0.3 to about 1 weight percent ammonium sulfate, based on the weight of the final herbicidal spray composition.

10. The method according to claim 7 wherein the herbicidal spray composition includes from about 0.001 to about 4 weight percent glyphosate, based on the weight of the final herbicidal spray composition.

11. A herbicidal aqueous spray composition comprising:

from about 0.05 to about 0.5 weight percent, based on the weight of the spray composition, of a liquid iminodipropionate amphoteric surfactant selected from the group consisting of C12-15 alkyloxypropyl-3-iminodipropionic acid, mono(sodium or potassium or ammonium) salt, decyloxypropyl-3-iminodipropionic acid, mono(sodium or potassium, or ammonium) salt {alternate name: beta.-alanine,N-(2-carboxyethyl)-N-[3-(decyloxy)propyl], mono(sodium or potassium or ammonium) salt}, and mixtures thereof;

from about 0.001 to about 4 weight percent, based on the weight of the spray composition of a herbicide selected from the group consisting of glyphosate, weak acid herbicides, and mixtures thereof;

from about 0.3 to about 1 weight percent, based on the weight of the spray composition, ammonium sulfate; and water.

* * * * *